United States Patent
Gmeiner

(12) 
(10) Patent No.: US 6,342,485 B1
(45) Date of Patent: Jan. 29, 2002

(54) SYNERGISTIC COMPOSITIONS USEFUL AS ANTI-TUMOR AGENTS

(76) Inventor: William H. Gmeiner, 1541 S. 190th St., Omaha, NE (US) 68154

( * ) Notice: Subject to any disclaimer, the term of this patent is extended or adjusted under 35 U.S.C. 154(b) by 0 days.

(21) Appl. No.: 09/418,711

(22) Filed: Oct. 15, 1999

(51) Int. Cl.⁷ .................................................. A61K 31/70
(52) U.S. Cl. ............................ 514/44; 514/43; 514/50; 514/51; 514/53; 514/54; 514/256
(58) Field of Search .............................. 514/43, 44, 50, 514/51, 53, 54, 256

(56) References Cited

U.S. PATENT DOCUMENTS

| | | | |
|---|---|---|---|
| 5,457,187 A | * | 10/1995 | Gmeiner et al. |
| 5,614,505 A | * | 3/1997 | Gmeiner et al. |
| 5,663,321 A | * | 9/1997 | Gmeiner et al. |
| 5,741,900 A | * | 4/1998 | Gmeiner et al. |

* cited by examiner

*Primary Examiner*—James O. Wilson
(74) *Attorney, Agent, or Firm*—Suiter & Associates PC; Scott C. Rand; William J. Breen, III

(57) ABSTRACT

A method for treating neoplastic disease in animals including humans comprises administering a first composition comprising a TS inhibitor and a second composition comprising a nucleic acid-directed chemotherapeutic agent, and a composition for treating neoplastic disease in animals including humans comprises a first composition comprising a TS inhibitor and a second composition comprising a nucleic acid-directed chemotherapeutic agent. In a preferred embodiments, the TS inhibitor is a homo-oligomer of FdUMP, and the nucleic acid-directed chemotherapeutic agent is 5-FU or a pro-drug thereof. In a further aspect, compositions of a homo-oligonucleotide of 5-fluoro-2'-deoxyuridine-5'-O-monophosphate (FdUMP) with 5-fluorouracil exhibit a synergistic biological effect on neoplastic cells when compared to the activity of the individual components, the compositions being useful in the treatment of cancer in animals, including humans.

28 Claims, 2 Drawing Sheets

US 6,342,485 B1

SYNERGISTIC COMPOSITIONS USEFUL AS ANTI-TUMOR AGENTS

GOVERNMENT RIGHTS

This invention was made in part with government support under grant number NCI-60612 and Cancer Center Support Grant NCI-36727, awarded by the National Cancer Institute. The government has certain rights in the invention.

FIELD OF THE INVENTION

The present invention relates generally to a composition of matter that exhibits a synergistic biological effect containing homo-oligonucleotides of 5-fluoro-2'-deoxyuridine-5'-O-monophosphate (FdUMP) and 5-fluorouracil (5-FU). In another aspect, the present invention relates to combination therapy exhibiting a synergistic anti-proliferative effect on cancer cells when compared to the activity of the individual compounds of this invention. The compositions of this invention are of use in the treatment of cancer in animals, including humans.

BACKGROUND OF THE INVENTION

Anti-metabolite nucleosides and nucleoside analogs have found widespread use in the treatment of cancer and other human diseases. One such nucleoside analog, 5-fluorouracil (5-FU) has been used continuously since its development in 1957 by Duusinski and Heidelberger (U.S. Pat. No. 2,802,005) for the treatment of solid tumors of the head and neck, breast, and colon. 5-FU was originally designed to work as an inhibitor of thymidylate synthetase (TS), the enzyme which converts deoxyuridine 5'-O-monophosphate (dUMP) to deoxythymidine 5'-O-monophosphate (dTMP). It is believed that 5-FU retards tumor expansion by causing thymidine pools to become depleted in rapidly proliferating tumor cells.

Protocols for the administration of 5-FU for treatment of human cancer involve infusion of the drug for long periods of time. 5-FU is rapidly metabolized and excreted with a half-life in-vivo of about 18 minutes. While 5-FU is an effective anti-cancer agent when metabolically activated to become an inhibitor of TS or incorporated into nucleic acids, its effectiveness is hampered by rapid metabolism and formation of 2-fluoro-β-alanine (FBAL) which is neurotoxic and cardiotoxic. For these reasons researchers and clinicians have long desired a method of increasing the therapeutic index and target specificity of 5-FU.

A variety of pro-drug forms of 5-FU have been developed to address the issues of cellular uptake, sustained release, organ distribution, and transdermal or intestinal uptake that are problematic for the native drug. One of the most widely studied pro-drug forms of 5-FU is 5'-deoxy-5-fluorouridine (DFUR). DFUR is converted to 5-FU by pyrimidine nucleoside phosphorylase but has better cellular uptake properties than 5-FU. Like 5-FU, DFUR also releases FBAL as a toxic metabolite. Other nucleoside analogues of FUr include Tegafur [(1-(2-tetrahydrofuryl)-5-fluorouracil], Ftorafir [R,S-1-(tetrahydro-2-furanyl)-5-fluorouracil] and a variety of 5-fluorocytidine derivatives.

A variety of polymeric forms of 5-fluorouridine have also been prepared to provide sustained release of 5-FU. In U.S. Pat. Nos. 5,457,187; 5,614,505; 5,663,321, and 5,741,900, each of which is incorporated herein in its entirety, there are disclosed homo-oligomeric 5-fluorouridine and 5-fluorodeoxyuridine useful as a polymeric drug delivery system for production of FdUMP. Disclosed are methods of both preparing and utilizing these compositions. The oligomeric compounds were shown to traverse the cellular membranes of a variety of cell lines and were degraded to an active form. Homo-oligomeric FdUMP is taught to be a more effective cytotoxic agent in cell culture on a per residue basis than is monomeric 5-fluorodeoxyuridine. Homo-oligomeric FdUMP is taught to have the advantages of a longer residence time in-vivo and greater cytotoxicity per residue of 5-fluorodeoxyuridine and it is taught that oligomeric 5-fluorodeoxyuridine is therapeutically useful at lower doses than are monomeric 5-fluorouridine, 5-fluorodeoxyuridine, and 5-fluorouracil, making delivery of FdUMP as FdUMP[N] more cost effective on a per dose basis and less neurotoxic and cardiotoxic than delivery in a monomeric form. The reduced neuro- and cardiotoxicity is a consequence of lower levels of 2-fluoro-p-alanine (FBAL) released from the lower effective dosage.

SUMMARY OF THE INVENTION

The present invention relates to composition for treating neoplastic disease in animals including humans comprising a first composition comprising a TS inhibitor and a second composition comprising a nucleic acid-directed chemotherapeutic agent, and a method for treating neoplastic disease in animals including humans comprising administering to a host animal having a neoplastic disease a first composition comprising a TS inhibitor and a second composition comprising a nucleic acid-directed chemotherapeutic agent. In a preferred embodiment, the TS inhibitor is a homo-oligomer of FdUMP. By "nucleic acid-directed chemotherapeutic agent" is meant a composition that inhibits the synthesis, processing or function of RNA and/or DNA. In preferred embodiments, the nucleic acid-directed chemotherapeutic agent is a nucleoside analog that is incorporated into and affects subsequent processing and/or function of RNA and/or DNA. In a particularly preferred embodiment, the nucleic acid-directed chemotherapeutic agent is 5-FU or a pro-drug thereof.

In a further aspect, it has now unexpectedly been found that pharmaceutical compositions comprising 5-FU and homo-oligomeric FdUMP in accordance with the present invention demonstrate increased anti-proliferative activity and are more active than compositions containing only the individual components. In particular, significant anti-proliferative activity of the compositions of the present invention was found for concentrations of FdUMP[10] which alone had no significant effect on the growth of the cells.

In one aspect, the present invention relates to a composition having a synergistic anti-proliferative effect on neoplastic animal cells, comprising a synergistically effective amount of a homo-oligomer of FdUMP and 5-FU. In an embodiment, the animal cells are mammalian cells. In a further embodiment, the animal cells are human cells. In an embodiment, the neoplastic cell is a solid tumor cell, and in a further embodiment, the neoplastic cell is colorectal, breast, and ovarian cancer cells. In an embodiment, the homo-oligomer of FdUMP ranges from 2 to 26 monomers. In further embodiments, the homooligomer of FdUMP ranges from 5–15 monomers. In still further embodiments, the homooligomer of FdUMP ranges from about 8–12 monomers. In still further embodiments, the homooligomer of FdUMP ranges from about 9–11 monomers, and most preferably, contains 10 monomers.

In another aspect, the present invention relates to a method for the treatment of neoplastic disease in animals comprising administering to an animal having a disease a synergistically effective amount of a homo-oligomer of FdUMP and 5-FU.

In still a further aspect, the present invention relates to a method for inducing apoptosis in a tumor cell, comprising the step of administering to a cell culture or animal host having said tumor cell a composition comprising a synergistically effective amount of a homo-oligomer of FdUMP and 5-FU.

It is to be understood that both the foregoing general description and the following detailed description are exemplary and explanatory only and are not restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The detailed description of the invention may be best understood when read in reference to the accompanying drawings wherein.

DETAILED DESCRIPTION OF THE INVENTION

Figure 1:
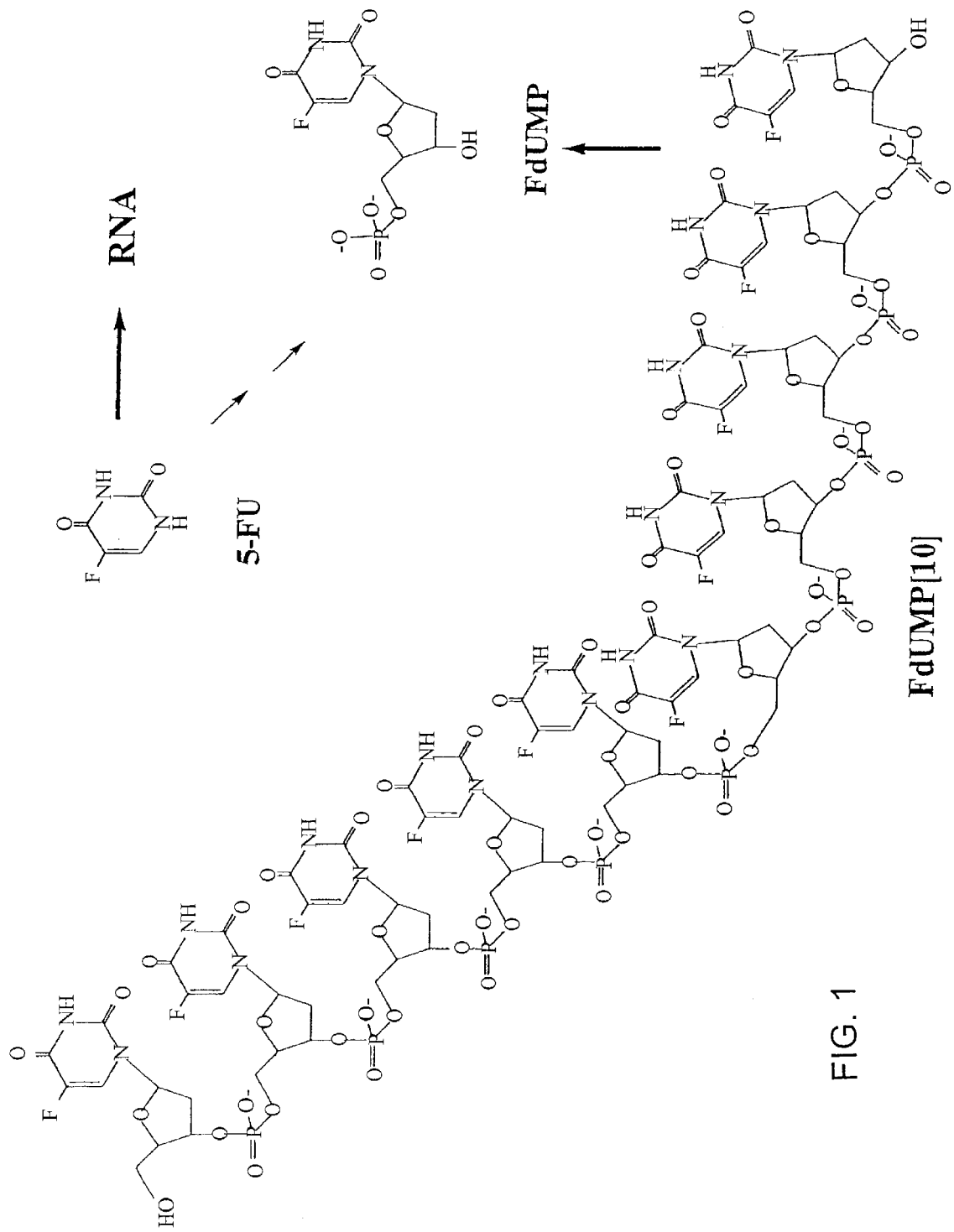
FIG. 1 illustrates the structure of FdUMP[10], the 10mer multimeric pro-drug of FdUMP. FdUMP is released from FdUMP[N] pro-drugs in a single-step catalyzed by enzymes having 3'→5' exonucleolytic activity, such as DNA polymerase I. 5-FU is also metabolized to FdUMP, but is also converted to numerous other intermediates, several of which have biological effects, such as FUTP which is incorporated into RNA as indicated in FIG. 1.

By "FdUMP[N]," is meant homo-oligomeric nucleotide, comprised of N number of monomers of FdUMP covalently attached via 3' to 5' phosphodiester linkages between the 5' phosphate of the 3' terminal FdUMP molecule and the 3' hydroxyl of the next attached FdUMP molecule with the terminating linkage being between the 5'-phosphate of the penultimate nucleotide and the 3'-hydroxyl of the terminating FdUMP molecule. The structure of FdUMP[10] is illustrated in FIG. 1.

By "anti-proliferation" is meant cytostatic and/or cytotoxic action upon cells. "Cytostatic" refers to the characteristic of suppressing the growth or multiplication of cells. "Cytotoxic" refers to the characteristic of having a specific toxic action upon cells of organs.

By "synergism" is meant that the combined action of two or more agents is greater than the sum of the actions of each of the agents used alone.

By "synergistically effective amount" is meant an amount of one component of the present invention sufficient to produce a synergistic anti-proliferative action when used in combination with another component or components of the present invention.

By "neoplasia" is meant the progressive multiplication of cells under conditions that would not elicit, or would cause cessation of, multiplication of normal cells. Thus, "neoplasm" refers to any new and abnormal growth, specifically, to a new growth of tissue in which the growth is uncontrolled and progressive. Malignant neoplasms are distinguished from benign in that the former show a greater degree of anaplasia and have the properties of invasion and metastasis (transfer of disease from one organ or part thereof to another not directly connected therewith). It will be appreciated that the therapeutic use of the present invention comprehends both malignant and benign neoplasia, with the preferred use in instances of malignant neoplasia.

Principles of neoplasia diagnosis and management are well known in the art. See, e.g., *Harrison's Principles of Internal Medicine*, Fauci et al., eds., 14th Edition, McGraw-Hill, New York, Chapters 81–101, pp. 493–618 (1997) and *Cecil Textbook of Medicine*, Bennett et al., eds., 20th Edition, W. B. Saunders Company, Philadelphia, Part XIV, Chapters 154–167, pp. 1004-77 (1996), incorporated herein by reference.

In one aspect, the present invention is directed to composition for treating neoplastic disease in animals including humans comprising a first composition comprising a TS inhibitor and a second composition comprising a nucleic acid-directed chemotherapeutic agent, and a method for treating neoplastic disease in animals including humans comprising administering to a host animal having a neoplastic disease a first composition comprising a TS inhibitor and a second composition comprising a nucleic acid-directed chemotherapeutic agent.

In one embodiment, the TS inhibitor is a homo-oligomer of FdUMP as described herein and in the above incorporated U.S. Pat. Nos. 5,457,187, 5,614,505; 5,663,321, and 5,741,900.

In one embodiment, the nucleic acid-directed chemotherapeutic agent is a nucleoside analog that is incorporated into and affects subsequent processing and/or function of RNA and/or DNA. In a particularly preferred embodiment, the nucleic acid-directed chemotherapeutic agent is 5-FU or a pro-drug thereof. Pro-drugs of 5-FU include, for example, DFUR, Tegafur, Ftorafur, and a variety of 5-fluorocytidine derivatives.

Synthesis of FdUMP[10]

FdUMP[10] was synthesized using standard methods for oligodeoxynucleotide (ODN) synthesis. This length was selected because previous studies on the dependence of the number, N, of FdUMP units in the multimer, FdUMP[N], had revealed that oligomers in this length range were effective in eliciting a biological response and this length permitted synthesis of high yields of full-length purified product. 5-Fluoro-2'-deoxyuridine (Sigma) was converted to 5'-O-(4,4'-Dimethoxytrityl)-5-Fluoro-2'-deoxyuridine 3'-(Cyanoethyl N, N-Diisopropylphosphoramidite) [FdU-amidite] according to standard procedures (Gmeiner et al., 1994). 5'-O-(4,4'-Dimethoxytrityl)-5-fluoro-2'-deoxyuridine was attached to controlled pore glass beads (CPG) using the procedure of Damha, et al., (Damha et al., 1990) and the derivatized controlled pore glass (CPG) was subsequently packed into 10 μmol columns. Each column was subjected to 9 coupling cycles with the FdU-amidite using the standard coupling cycle for the ABI 380-B DNA synthesizer. FdUMP [10] were then cleaved from the solid support by treatment with ammonium hydroxide followed by desalting with Sephadex G-25 column chromatography. Further purification was accomplished using polyacrylamide gel electrophoresis (PAGE; 20% gel). The gel-purified FdUMP[10] was desalted using size-exclusion chromatography and analyzed by mass spectrometry. The concentrations of FdUMP[10] solutions were determined from measurements of their absorbance at 260 nm using the conversion 33 $\mu$g/ODU. The concentrations of solutions of 5-FU (Sigma) were determined using a value of $7.07 \times 10^3 M^{-1} cm^{-1}$ for the molar extinction coefficient.

The homo-oligomers of FdUMP may conjugated with lipophilic moities at either the 3' or the 5' terminal hydroxyl to enhance cellular uptake. Lipophilic moieties include, for example, cholesterol or cationic amino acids such as L-lysine or poly-L-lysine. Such derivitization has proven useful in studies with other oligonucleotides in improving cellular uptake above the relatively good uptake of the native oligonucleotides. Such conjugation increases the affinity of the oligonucleotides for the cellular membrane or reduces electrostatic repulsions for the oligonucleotide while in the hydrophobic membrane or possibly promotes cellular uptake via receptors that recognize the conjugated species. The presence of lipophilic or cationic moieties at the termini effects subcellular distribution and metabolism. In particular, 3'-terminus derivatization hinders 3'-exonuclease activity and retards the enzymatic degradation of FdUMP[N]. Preferably a preparation of FdUMP[N] with cholesterol, ethyl-spaced adamantane, and 1,2-di-hexadecyl glycerol at either the 5' or the 3' termini are utilized. Homo-oligomers of FdUMP conjugated with lipophilic moieties may be prepared as taught by the incorporated U.S. Pat. Nos. 5,457,187; 5,614,505; 5,663,321; and 5,741,900.

The anti-proliferative (cytostatic/cytotoxic) activity of admixtures of FdUMP[10] and 5-FU was determined as follows.

MTT Assay

The antiproliferative activities of FdUMP[10] and 5-FU for the human colorectal tumor cell lines H630 and H630-10 were compared using an assay for 3-(4,5-dimethylthiazol-2-yl)-2,5-diphenyltetrazolium bromide (MTT). H630 and H630-10 cells were cultured using RPMI 1640 containing L-glutamine and supplemented with 10% Nu-serum IV. All culture media were supplemented with penicillin/streptomycin. 25,000 cells were plated (96 well flute-bottom plate) in 200 $\mu$L of medium at 37° C. overnight in an air atmosphere containing 5% $CO_2$. The medium was replaced the next day, and cells were exposed to the drugs for 24 h. The medium was then removed from the plates and replaced with 100 $\mu$L of fresh medium and 25 $\mu$L of MTT solution (5 $\mu$g/$\mu$L in PBS) per well. Following 2 h incubation, 100)L of MTT solvent (20% w/v SDS dissolved in DMF:$H_2O$ [1:1], pH 4.7) was added to each well and the plates were incubated overnight (Senderoff et al., 1990). The plates were analyzed the following morning on a Titerek Multiscan Plus 96-well plate analyzer (v.1.4). The number of viable cells in each well containing cells treated with drug was calculated from the absorbance at 570 nm compared to untreated controls. The means and standard deviation at each concentration for each drug were calculated using standard statistical methods. MTT assays were run in duplicate or triplicate to assure the statistical significance of the results.

Clonogenic Assay.

About one thousand viable H630 or H630-10 cells suspended in 10 mL of RPMI 1640 medium with 9% NU serum IV were grown at 37° C. in a humidified 5% $CO_2$-air atmosphere in 100×20 mm plastic petri dishes. After 48 h, the medium was removed, and replaced with 10 mL of fresh medium containing either 5-FU, FdUMP[10], or both 5-FU and FdUMP[10]. After 72 h, the medium containing drugs was removed and replaced by fresh medium. Plates were incubated for 2 to 3 weeks with fresh medium added, if necessary, after which the medium was removed, and the clones were identified by staining with 0.1% methylene blue in 70% ethanol aqueous solution. The number of surviving colonies was counted, and calculated as a percent of controls. Each study was repeated twice.

Induction of Apoptosis by FdUMP[10].

A TUNNEL assay was used to determine if exposure of H630 cells to FdUMP[10] resulted in apoptosis. About one million H630 cells were seeded into each of the T-75 cell culture flasks. Two days later, after two doubling times, the cells were exposed to FdUMP[10]. The cells were exposed to FdUMP[10] for 72 h, and then fixed with 1% methanol-free formaldehyde for 20 min at 0° C. The fixed-cells were then placed in a 70% ethanol solution at −20° C. for two weeks. The ethanol was then removed, and the cells were washed with PBS and incubated with TdT buffer (Promega), containing equilibration buffer, nucleotide mixture and TdT enzyme, at 37° C. for 1 hour. The reaction was terminated by addition of EDTA solution and the incubation buffer was then removed. The cells were then treated with 0.1% Triton, followed by propidium iodide containing DNAse-free RNAse. The cells were kept at room temperature for 30 min, and then analyzed by flow cytometry.

Interaction of FdUMP[10] and 5-FU

The ability of FdUMP[10] and 5-FU to interact in a positive manner to inhibit the proliferation of H630 and H630-10 cells was evaluated by combining the drugs during the exposure period of the MTT or clonogenic assay, and evaluating the viability of the cells exposed to the combination of drugs by absorbance at 570 nM (MTT assay), or by counting the number of surviving colonies (clonogenic assay). The concentrations of FdUMP[10] used in combination with 5-FU (4.0 and $6.0 \times 10^{-8}$) were not growth inhibitory to the target cells when administered as a single agent.

Inhibition of H630 Cells by FdUMP[10], 5-FU.

Fluorinated pyrimidines are frequently used in the treatment of human colorectal cancer. In order to determine if FdUMP[10] and 5-FU interact in a positive manner to arrest the proliferation of human colorectal tumor cells, the antiproliferative activities of FdUMP[10] and 5-FU were first evaluated independently. Proliferation of H630 and H630-10 human colorectal tumor cells was monitored using MTT and clonogenic assays. H630-10 cells are derived from H630 cells by culturing in media containing 5-FU, and they overexpress TS about 30-fold relative to H630 cells (Copur et al., 1995). The $IC_{50}$ values for 5-FU and FdUMP[10] towards H630 and H630-10 cells using both assays are shown in Table 1. The data clearly show that both FdUMP[10] and 5-FU are effective at reducing the number of viable cells in culture in a concentration-dependent manner. It is also evident from the data that FdUMP[10] is considerably more effective at reducing cell viability than are similar concentrations of 5-FU. In fact, the efficiency of FdUMP[10] as monitored using an MTT assay is about 400 times that of 5-FU, a value too large to be explained by the ten-fold excess of fluorinated pyrimidine in FdUMP[10] relative to 5-FU. FdUMP[10] is also considerably more effective than 5-FU towards H630, and particularly H630-10 cells, as measured using a clonogenic assay.

TABLE 1

$IC_{50}$ Values for 5-FU and FdUMP[10] Towards H630 and H630-10 Cells.

| Cell Line | MTT Assay | | Clonogenic Assay | |
|---|---|---|---|---|
| | 5-FU[a] | FdUMP[10][b] | 5-FU | FdUMP[10] |
| H630 | $4.87 \times 10^{-6}$ | $1.69 \times 10^{-8}$ | $3.90 \times 10^{-6}$ | $2.50 \times 10^{-7}$ |
| H630-10 | $2.71 \times 10^{-5}$ | $9.95 \times 10^{-8}$ | $7.50 \times 10^{-5}$ | $7.10 \times 10^{-8}$ |

[a]Errors ± $2 \times 10^{-6}$
[b]Errors ± $1 \times 10^{-8}$

Establishment of FdUMP[10] as being more effective than 5-FU at inhibiting proliferation of H630 and H630-10 cells in both MTT and clonogenic assays raises the issue of the fate of these cells when exposed to FdUMP[10]. The induction of apoptosis by FdUMP[10] in H630 cells was explored using a TUNEL assay. TUNEL staining revealed a dose-dependent induction of apoptosis in H630 cells with essentially 100% of cells exposed to the drug undergoing apoptosis (data not shown). These results clearly demonstrate that FdUMP[10] is a cytotoxic agent that efficiently induces apoptosis in cells exposed to the drug. Preliminary experiments indicate the mechanism(s) of cytotoxicity for FdUMP[10] are complex. Deoxythymidine does not rescue cells from FdUMP[10], and may actually enhance the drugs potency. In contrast, uridine appears to partially reverse the effects of FdUMP[10]. Detailed studies of the mechanism(s) of cytotoxicity by FdUMP[10] are in progress.

Positive Interaction of FdUMP[10] and 5-FU

Figure 2:
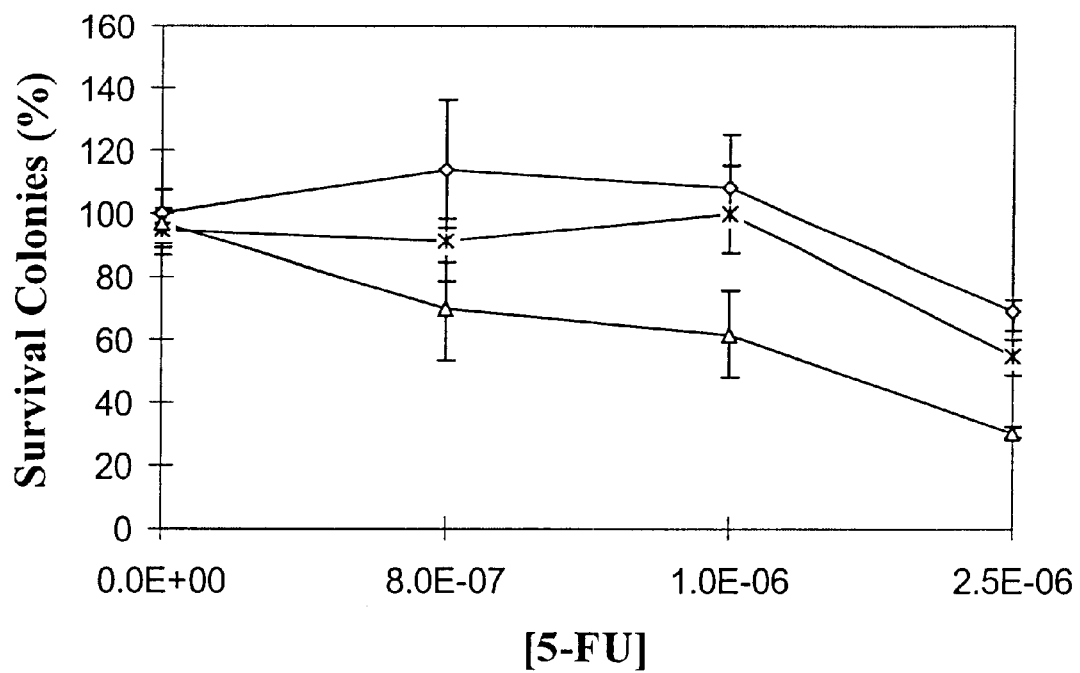
FIG. 2 illustrates the synergistic interaction of FdUMP[10] and 5-FU at inhibiting proliferation of human colorectal tumor cells (H630) measured using a clonogenic assay. Three growth inhibition curves are shown. The top curve (diamond) indicates the effects of 5-FU alone. The middle (x) and bottom (triangle) curves indicates the effect of 5-FU combined with a $4.0\times10^{-8}$ and $6.0\times10^{-8}$ M concentrations of FdUMP[10], respectively. Incubation with $4.0\times10^{-8}$ and $6.0\times10^{-8}$ M concentrations of FdUMP[10] alone had no significant effect on the growth of H630 cells. Standard deviations were obtained from four independent experiments.

The principal cellular target of fluorinated pyrimidine chemotherapy is TS inhibition. 5-FU is known to have alternative deleterious mechanisms in addition to TS inhibition, particularly RNA-mediated effects, that likely contribute to its anticancer activity. To explore potential interactions between 5-FU and FdUMP[10], the viability of H630 cells exposed to a combination of the drugs was analyzed using MTT and clonogenic assays. Specifically, a single concentration of FdUMP[10] was selected for each experiment, and this dose was co-administered with one of a range of 5-FU doses. The FdUMP[10] concentrations selected (4.0 and $6.0 \times 1^{-8}$ M) had no significant antiproliferative activity as single agents towards these cells. In all cases, the observed activity of 5-FU was markedly enhanced by combination with FdUMP[10]. These results are displayed graphically in FIG. 2.

Over the last two decades, a number of studies have indicated that chemotherapy with 5-FU in combination with other drugs improves long-term survival of patients with colon cancer. For instance, in 1988, an improvement in disease-free survival and overall survival of 8% was demonstrated at 5 years of follow up for patients with stages II and III colon cancer treated with post-operative chemotherapy consisting of 5-fluorouracil (5-FU), semustine, and vincristine (MOF regimen) (Wolmark et al., 1992). However, after 8 years of follow-up, this benefit was no longer apparent. In 1990, a large multicenter trial of 5-FU/levamisole reported prolonged disease-free and overall survival in patients with stage III colon cancer, compared with patients who received no treatment after surgery (Moertel et al., 1990). This benefit has persisted with continued follow-up (Moertel et al., 1995). More recently, the National Surgical Adjuvant Breast and Bowel Project (NSABP) reported a trial of stage II and III patients comparing the original MOF regimen to a weekly regimen of 5-FU plus high-dose leucovorin. This demonstrated a statistically significant benefit for 5-FU/leucovorin in both overall and disease-free survival (Wolmark et al., 1993). Taken together, randomized trials comparing adjuvant chemotherapy to surgery alone have shown a reduction in mortality of between 22% and 33% using protocols containing 5-FU.

The principal mechanism responsible for the antitumor activity of 5-FU involves metabolic conversion to FdUMP, a potent inhibitor of TS (Santi et al., 1974). Exposure of cells to 5-FU depletes cellular pools of dTTP resulting in cytostasis, and in certain instances, apoptosis. Exposure of cells in culture to 5-FU results in a cytostatic condition referred to as "thymineless cell death" (Weckbecker, 1991; Houghton et al, 1994). Simultaneous exposure of cells in culture to both 5-FU and dTMP also results in cytostasis implicating non-TS inhibitory processes in the growth inhibitory activity of 5-FU (Spiegelman et al, 1980). The longstanding and widespread utility of 5-FU as a clinically useful chemotherapeutic agent arises, in part, from the occurrence of mechanisms other than TS inhibition. In particular, 5-FU is metabolized to FUTP and FdUTP and incorporated into RNA and DNA, respectively (Weckbecker, 1991). The incorporation of FdUTP into cellular DNA occurs only after depletion of cellular dTTP stores as a result of TS inhibition by FdUMP. The incorporation of FUTP into cellular RNA occurs readily and no repair processes are known that remove FUrd from RNA. The antineoplastic activity of FUrd correlates well with the amount of FUrd incorporated into cellular RNA, at least in some instances (Matsuoka et al., 1992). Incorporation of FUrd into RNA may also contribute substantially to the toxicity of 5-FU as it is expected to affect both proliferating and non-proliferating cells. Our laboratory has reported a number of studies that indicate the 5-FU affects the structure and stability of duplex DNA and RNA stem-loops (Sahasrabudhe et al., 1995; Sahasrabudhe et al., 1996; Sahasrabudhe and Gmeiner, 1997). FdUMP[N] compounds have a number of similarities to 5-FU as well as a number of differences. Obviously, both are forms of fluorinated pyrimidine that are capable of being converted to the TS inhibitory nucleotide FdUMP. FdUMP[N] however, have the biochemical and pharmacological properties of antisense oligonucleotides, including high molecular weight and charge (Crooke 1992). 5-FU, in contrast, is a small neutral molecule. The pharmacological and biochemical properties of 5-FU and FdUMP[N] may be thought of as complementary and it has been found in accordance with the present invention that their combined use in the treatment of human cancer is more effective than the current use of 5-FU, either alone or in combination with modulating agents such as leucovorin. In the present study we report that FdUMP[10] interacts with 5-FU in a positive manner to arrest proliferation of cultured human colorectal tumor cells. This evidence, along with evidence from our laboratory that indicate FdUMP[N] compounds are well-tolerated in vivo, provide an encouraging starting point for the pursuit of studies to investigate the antitumor activity of FdUMP[N] in vivo (Liu et al., 1999).

It was found that a combination of FdUMP[10] with 5-FU has a higher cytostatic and/or cytotoxic effect than could be expected from adding together the effects of the individual components, i.e., an unexpected synergistic antiproliferative effect was observed when the combination was used.

These results demonstrate that in vitro anti-proliferative (cytostatic/cytotoxic) effects can be achieved with the described compositions which would otherwise be achievable only by the use of extremely high doses of the individual components, and which would be intolerable due to adverse toxic side effects, or in some cases which could be achieved even with high doses of the individual components of the compositions described.

The synergistic compositions in accordance with this teaching exhibit profound effects on the inhibition of growth of cancer cell lines and tumors including but not limited to colorectal, breast, ovarian cancers. Other cancers that may be treated by the compositions in accordance with the present invention include, but are not limited to, non-small cell lung cancer, CNS cancer, melanoma, renal cancer, prostate cancer, leukemia, cancers of the head and neck, and cancers of other body organs. The compositions of the present invention can be administered to animal cells, including human cells, in vivo or in vitro.

Thus, administration to a patient suffering from a neoplastic disease can be intraperitoneal (if disease is at a stage where ascites fluid is present), intratumoral or by injection (if a mass is present), or by infusion into a tumor-adjacent artery. Dosages will depend on the age of the patient, side effects, condition of the patient, advanced stage of the carcinoma, and other such factors readily determined by those skilled in the art. Also within the contemplation of the present invention is the administration of the respective compounds as a continuous infusion, in order to maintain relatively constant blood and/or tissue concentrations at such a level as one of skill in the art will consider desirable given the condition of the patient and other such factors as described above.

The term "administer" includes any and all means by which an effective amount of the active agents can be introduced into the system of the animal to be treated. Such methods include but are not limited to oral administration, topical administration, as well as administration parenterally, the active agent or agents dissolved in or compounded with a suitable pharmaceutical carrier. The compounds can be employed in dosage forms such as tablets, capsules, powder packets, or liquid solutions, suspensions or elixirs if used for oral administration. Sterile liquid formulations such as suspensions or solutions can be prepared for parenteral use. In such compositions the active agent or agent will normally be present in an amount of at least 0.5% by weight, based on the weight of the composition, and up to 99.5% by weight thereof. Intramuscular intravenous and intraperitoneal injections are the preferred methods of introducing the active agents of the present invention.

The compounds of the present invention may be administered together or separately in a manner allowing control of the dosage at the target cells, and to optimize the therapeutic effect thereof. For example, if the components of the present invention are administered separately, the administration may be simultaneous, alternate, in parallel, continuous, or a combination of the above, as the practitioner of skill considers indicated in the particular case. Of course, if the components of the present invention are administered together, their relative proportions may be adjusted according to the needs of the patient to whom administered.

The compounds of the present invention may be administered by any means effecting palliating conditions in animals. For example, administration may be parenteral, i.e., subcutaneous, intravenous, intramuscular, or interperitoneal. Parenteral compositions suitable for the practice of the present invention include the active agents in combination with a pharmaceutically acceptable carrier, solvent, or diluent. Typical vehicles for parenteral administration of the active ingredients include aqueous vehicles, water-miscible vehicles such as ethyl alcohol, polyethylene glycol and polypropylene glycol, and nonaqueous vehicles such as oil-based vehicles, e.g., vegetable oils, ethyl oleate, isopropyl myristate and benzyl benzoate. Typical parenteral preparations are described in *Remington's Pharmaceutical Sciences*, Mack Publishing Company, Easton, Pa., latest edition.

Therapeutic methods of use of the present invention comprehend administering to target cells synergistically effective amounts of FdUMP[10] and 5-FU by methods including but not limited to those described herein, said target cells being located in vivo, in situ, and/or in vitro. Synergistically effective amounts of FdUMP[10] will preferably range from about from about 5 to about 250 mg/kg body weight, more preferably from about 5 to about 150 mg/kg, and most preferably from about 20 to about 50 mg/kg body weight. Synergistically effective amounts of 5-FU will preferably range from about 5 to about 30 mg/kg body weight, more preferably from about 10 to about 20 mg/kg body weight. It will be appreciated that the actual dosages used in the treatment of neoplasias will vary according to the mode of administration, the condition of the patient and other factors including but not limited to those described herein, as would be understood by those skilled in the art. The dosages and regimens, formulation, and administration methods employed will be determined by a skilled clinician and may be generally comparable to those known for the individual components. It will be recognized, however, that the dosage levels and/or frequency of administration may be reduced as compared to the individual components in view of the synergistic biological effect of the composition in accordance with this teaching.

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents.

REFERENCES

Each of the following references is incorporated herein by reference in its entirety:

Copur et al., "Thymidylate synthase gene amplification in human colon cancer cell lines resistant to 5-fluorouracil," *Biochem. Pharnacol.*, 49: 1419–1426 (1995).

Crooke, "Therapeutic applications of oligonucleotides," *Annu. Rev. Pharmacol Toxicol.*, 32: 329–376 (1992).

Damha et al., "An improved procedure for derivatization of controlled-pore glass beads for solid phase oligonucleotide synthesis," *Nucl. Acids Res.*, 18: 3813–3821 (1990).

Gmeiner et al., "Preparation of oligomeric 2'-deoxy-5-fluorouridylate of defined length and backbone composition: a novel pro-drug form of the potent anti-cancer drug 2'-deoxy-5-fluorouridylate," *Nucl. Nuct.*, 14: 243–253 (1995).

Gmeiner, "Delivery of traditional anti-cancer drugs as oligodeoxynucleotides," *Cancer Watch*, 4: 120–121 (1995).

Gmeiner et al., "Synthesis of 5'-O-(4,4'-Dimethoxytrityl)-2'-O-(tert-butyldimthylsilyl)-5-fluorouridine 3'-(Cyanoethyl N,N-diisopropylphosphoramidite) and its use in the synthesis of RNA," *J. Org. Chem.*, 59: 5779–5783 (1994).

Houghton et al., "Cell cycle control processes determine cytostasis or cytotoxicity in thymineless death of colon cancer cells," *Cancer Res.*, 54: 4967–4973 (1994).

Houghton et al., "Relationship between 5-fluoro-2'-deoxyuridylate, 2'-deoxyuridylate, and thymidylate synthetase activity subsequent to 5-fluorouracil administration, in xenografts of human colon adenocarcinomas," *Biochem. Pharmacol.* 35:1351–1358 (1986).

Liu et al., "Increased cytotoxicity and decreased in vivo toxicity of FdUMP[10] relative to 5-FU," *Nucl. Nuct.*, 18:1789–1802 (1999).

Matsuoka et al., "Preliminary evidence that incorporation of 5-fluoruracil into RNA correlates with antitumor response," Cancer Invest. 10: 265–269 (1992).

Moertel et al., "Levamisole and fluorouracil for adjuvant therapy of resected colon carcinoma," *N. Eng. J Med.*, 322: 352–358 (1990).

Moertel et al., "Fluorouracil plus levamisole as effective adjuvant therapy after resection of stage III colon carcinoma: a final report," *Ann. Int. Med.*, 122: 321–326 (1995).

Parker et al., "Metabolism and mechanism of action of 5-fluorouracil," *Pharmac. Ther.*, 48: 383–395 (1990).

Pratt et al. (Eds.), *The Anticancer Drugs*, 2nd edition, Oxford Press, New York, pp. 69–107 (1994).

Sahasrabudhe et al., "Solution structures of 5-fluorouracil-substituted RNA duplexes containing G-U wobble base pairs," *Biochemistry*, 36: 5981–5991 (1997).

Sahasrabudhe et al., "Solution structures of 5-fluorouracil-substituted DNA and RNA decamer duplexes," *Biochemistry*, 35: 13597–13608 (1996).

Sahasrabudhe et al., "Effects of site-specific substitution of 5-fluorouridine on the stabilities of duplex DNA and RNA," *Nucl. Acids Res.* 23, 3916–3921 (1995).

Santi et al., "5-Fluoro-2'-deoxyuridylate covalent complex with thymidylate synthase," *Proc. Natl. Acad. Sci. USA*, 69: 1855–1857 (1972).

Senderoff et al. "Evaluation of anti-proliferative agents using a cell-culture model," *Invest. Opthamol. Vis. Sci.*, 31: 2572–2578 (1990).

Spiegelman et al., "Improving the anti-tumor activity of 5-fluorouracil by increasing its incorporation into RNA via metabolic modulation," *Cancer* (Phila.): 45, 1129–1134 (1980).

Tew et al., *Preclinical and Clinical Modulation of Anticancer Drugs*, CRC Press, Boca Raton (1991).

Weckbecker, "Biochemical pharmacology and analysis of fluoropyrimidines alone and in combination with modulators," *Pharmac. Ther.*, 50: 367–424 (1991).

Wolmark et al., "Postoperative adjuvant chemotherapy or BCG for colon cancer: results from NSABP protocol C-01," *J Natl. Cancer Inst.*, 80: 30–36 (1992).

Wolmark et al., "The benefit of leucovorin-modulated fluorouracil as postoperative adjuvant therapy for primary colon cancer: results from National Surgical Adjuvant Breast and Bowel Project protocol C-03," *J Clin. Oncol.*, 11: 1879–1887 (1993).

What is claimed is:

1. A composition for treating neoplastic disease in animals comprising synergistically effective amounts of the nucleic acid directed chemotherapeutic compound 5-FU and a TS inhibitor compound which is a homo-oligomer of FdUMP, wherein the homo-oligomer is comprised of 2 to 26 FdUMP monomers.

2. A composition according to claim 1, wherein the nucleic acid-directed chemotherapeutic agent is a pro-drug of 5-FU.

3. A method for treating neoplastic disease in animals comprising administering to a host animal having a neoplastic disease a composition comprising synergistically effective amounts of the nucleic acid directed chemotherapeutic compound 5-FU and a TS inhibitor compound which is a homo-oligomer of FdUMP, wherein the homo-oligomer is comprised of 2 to 26 FdUMP monomers.

4. A method according to claim 3, wherein the nucleic acid-directed chemotherapeutic agent is a nucleoside analog that is incorporated into and affects subsequent processing and/or function of RNA and/or DNA.

5. A method according to claim 3, wherein the nucleic acid-directed chemotherapeutic agent is a pro-drug of 5-FU.

6. A composition having a synergistic anti-proliferative effect on neoplastic animal cells, comprising synergistically effective amounts of 5-FU and a homo-oligomer of FdUMP, wherein the homo-oligomer is comprised of 2 to 26 FdUMP monomers.

7. A composition of claim 6 having a synergistic anti-proliferative effect on neoplastic animal cells, wherein said neoplastic animal cell is a solid tumor cell, said composition comprising synergistically effective amounts of 5-FU and a homo-oligomer of FdUMP.

8. A composition of claim 6 having a synergistic anti-proliferative effect on neoplastic animal cells selected from the group consisting of colorectal, breast, and ovarian cancers, said composition comprising synergistically effective amounts of 5-FU and a homo-oligomer of FdUMP.

9. A composition according to claim 6, wherein said homo-oligomer of FdUMP consists essentially of 5 to 15 FdUMP monomers.

10. A composition according to claim 6, wherein said homo-oligomer of FdUMP consists essentially of 8 to 12 FdUMP monomers.

11. A composition according to claim 6, wherein said homo-oligomer of FdUMP consists essentially of 9 to 11 FdUMP monomers.

12. A composition according to claim 6, wherein said homo-oligomer of FdUMP consists essentially of 10 FdUMP monomers.

13. A composition according to claim 7, wherein said homo-oligomer of FdUMP consists essentially of 5 to 15 FdUMP monomers.

14. A composition according to claim 7, wherein said homo-oligomer of FdUMP consists essentially of 8 to 12 FdUMP monomers.

15. A composition according to claim 7, wherein said homo-oligomer of FdUMP consists essentially of 9 to 11 FdUMP monomers.

16. A composition according to claim 7, wherein said homo-oligomer of FdUMP consists essentially of 10 FdUMP monomers.

17. A composition according to claim 8, wherein said homo-oligomer of FdUMP consists essentially of 5 to 15 FdUMP monomers.

18. A composition according to claim 8, wherein said homo-oligomer of FdUMP consists essentially of 8 to 12 FdUMP monomers.

19. A composition according to claim 8, wherein said homo-oligomer of FdUMP consists essentially of 9 to 11 FdUMP monomers.

20. A composition according to claim 8, wherein said homo-oligomer of FdUMP consists essentially of 10 FdUMP monomers.

21. A pharmaceutical formulation comprising a composition according to claim 6 and a pharmaceutical excipient.

22. A pharmaceutical formulation comprising a composition according to claim 7 and a pharmaceutical excipient.

23. A pharmaceutical formulation comprising a composition according to claim 8 and a pharmaceutical excipient.

24. A pharmaceutical formulation comprising a composition according to claim 18 and a pharmaceutical excipient.

25. A pharmaceutical formulation comprising a composition according to claim 16 and a pharmaceutical excipient.

26. A pharmaceutical formulation comprising a composition according to claim 20 and a pharmaceutical excipient.

27. A method of inducing apoptosis in a tumor cell comprising the step of administering to a cell culture or animal host having said tumor cell a composition comprising a synergistically effective amounts of 5-FU and a homo-oligomer of FdUMP, wherein the homo-oligomer is comprised of 2 to 26 FdUMP monomers.

28. A composition according to claim 1, wherein the nucleic acid-directed chemotherapeutic agent is a nucleoside analog that is incorporated into and affects subsequent processing and/or function of RNA and/or DNA.

* * * * *